(12) United States Patent
Wilbers (10) Patent No.: US 7,231,871 B1
(45) Date of Patent: Jun. 19, 2007

(54) BAKING APPARATUS AND METHOD FOR BAKING EDIBLE PRODUCTS

(75) Inventor: Wilhelmus Johannes E. M. Wilbers, Udenhout (NL)

(73) Assignee: Wegra Beheer B.V., Valkenswaard (NL)

( * ) Notice: Subject to any disclaimer, the term of this patent is extended or adjusted under 35 U.S.C. 154(b) by 0 days.

(21) Appl. No.: 10/203,466

(22) PCT Filed: Feb. 10, 2000

(86) PCT No.: PCT/NL00/00083

§ 371 (c)(1),
(2), (4) Date: Oct. 21, 2002

(87) PCT Pub. No.: WO01/58269

PCT Pub. Date: Aug. 16, 2001

(51) Int. Cl.
*A47J 37/01* (2006.01)

(52) U.S. Cl. .......................... 99/325; 99/326; 99/329 P; 99/331; 99/337; 99/338; 99/344; 99/451; 99/474

(58) Field of Classification Search .... 99/325–329 RT, 99/337–338, 342–344, 467, 474, 451
See application file for complete search history.

(56) References Cited

U.S. PATENT DOCUMENTS

| | | | |
|---|---|---|---|
| 3,697,725 A | * | 10/1972 | Bielefeldt .................. 219/388 |
| 3,886,539 A | * | 5/1975 | Gould, Jr. .................... 345/173 |
| 3,917,445 A | | 11/1975 | Suvá et al. |
| 3,936,702 A | * | 2/1976 | Plasko ......................... 361/104 |
| 4,251,716 A | * | 2/1981 | Lewis et al. ............. 219/445.1 |
| 4,353,929 A | | 10/1982 | Flavan, Jr. et al. |
| 4,565,704 A | * | 1/1986 | Dagerskog et al. ......... 426/233 |
| 4,621,310 A | * | 11/1986 | Keating ...................... 362/344 |
| 5,179,265 A | * | 1/1993 | Sheridan et al. ............ 219/497 |
| 5,223,290 A | * | 6/1993 | Alden ........................ 426/243 |

FOREIGN PATENT DOCUMENTS

| | | | |
|---|---|---|---|
| EP | 1074186 A2 | * | 2/2001 |
| GB | 1551516 A | * | 8/1979 |
| JP | 403048392 A | * | 3/1991 |
| JP | 05-190472 | * | 7/1993 |
| JP | 05 190472 A | | 7/1993 |
| JP | 409048640 A | * | 2/1997 |
| NL | 1 009 838 C | | 2/2000 |
| WO | WO 94 24502 A | | 10/1994 |

* cited by examiner

*Primary Examiner*—Drew Becker
(74) *Attorney, Agent, or Firm*—Hoffmann & Baron, LLP (57) ABSTRACT

Baking apparatus for baking edible products located on a conveying surface and preferably travelling along a conveyor track, comprising a number of electric infrared radiators arranged above the conveyor track. The infrared radiators each comprise at least one spiral filament having a gastight, infrared radiation-transmitting, breakable casing, in particular a glass casing. The baking apparatus further comprises monitoring means for monitoring breakage of the casings of the infrared radiators. The invention also relates to a method for baking an edible product by means of an electric infrared radiator having a breakable casing.

21 Claims, 4 Drawing Sheets

BAKING APPARATUS AND METHOD FOR BAKING EDIBLE PRODUCTS

This application is the U.S. National Phase of International Application Number PCT/NL00/00083 filed on 10 Feb. 2000, which is incorporated herein by reference.

BACKGROUND OF THE INVENTION

The invention relates to a baking apparatus for baking edible products located on a conveying surface and preferably traveling along a conveyor track.

It is observed that in this context, "baking" should be understood to mean at least the complete or partial browning and/or the complete or partial cooking of a product.

In the food industry, there is currently an increasing interest for products which are ready to be consumed by a consumer or which require only a short preparation time for consumption. Examples hereof are pastas or pieces of meat which are completely or partially pre-baked and which can be prepared by a consumer by heating briefly, for instance by heating in a microwave oven.

During manufacture of such products, it is important that the baking process can be accurately controlled. With so-called ready-to-eat meals, it is for instance important that the different components of the meal be pretreated in such a manner that the remaining preparation time of the components is substantially the same and that after a brief preparation by the consumer, each of the components of the meal has the proper degree of cooking. In the case of perishable products, it is further important that it can be predicted with great certainty which degree of cooking is reached, because the storage life of the product, i.e. the safe time interval between the moment when the product is prebaked and the moment when it should have been consumed, can thereby be increased. In particular for meat products, at least meat-containing products, the above problems play a substantial part.

Conventionally, products, for instance pieces of meat, are prebaked by moving them through a trough of boiling oil by means of a conveyor track. A drawback hereof is that the baking process cat be controlled fast enough. In particular, the temperature of the oil cannot be adjusted fast enough when, suddenly, many products are immersed in the oil or when, suddenly, the size of the products to be baked varies. Consequently, as far as the degree of cooking is concerned, there should always be observed an ample safety margin, as a result of which the storage life of a product is relatively short and a product, after preparation by a consumer, is often overdone.

Further, a drawback of baking with oil is that a product loses relatively much moisture during baking. This reduces the weight of the product, thereby increasing the costs per unit of weight of the end product. Further, an oil-baked product contains relatively much fat, which is currently usually considered undesirable by the consumer. In additions the oil affects the taste of the product, as a result of which high requirements have to be imposed on the quality of the oil. Consequently, the oil has to be replaced often. This does not only have the drawback that large quantities of new oil have to be purchased, but also that large amounts of fouled oil have to be discharged. Moreover, keeping the oil at the proper temperature requires relatively much energy.

To avoid these drawbacks, it has already been proposed, for instance, to precook pieces of meat by means of steam. A drawback hereof is that the meat assumes an grey color, which is usually experienced as unappealing by the consumer. Particularly for products which are to be consumer-prepared by microwave oven only, this grey appearance has proved to be a major problem from the point of view of selling.

SUMMARY OF THE INVENTION

The object of the invention is to provide a baking apparatus for baking edible products traveling along a conveyor track, which apparatus does not have the above-mentioned drawbacks. To that end, a baking apparatus according to the invention is characterized in that it comprises a number of electric infrared radiators arranged above the conveyor track, each infrared radiator comprising at least one spiral filament having a gastight, infrared radiation-transmitting, breakable casing, in particular a glass casing, and further comprises monitoring means for monitoring breakage of at least one of the casings.

The effect achieved through the use of infrared radiation is that an edible product can be baked contactlessly. Thus, the use of oil can be minimized or even be omitted completely, while the product obtains an appealing appearance all the same. Through the use of a gastight casing of the spiral filament, it is achieved that a spiral filament can be used of which the intensity of the emitted radiation is quickly and accurately settable, so that the baking process can be controlled very effectively. In particular, the supply of radiation can thus be controlled so that radiation is supplied only when needed, which enables energy saving. Further, the degree of cooking of a product can thus be properly predicted. A further advantage of the casing is that it protects the spiral filament, for instance against fouling. The use of monitoring means prevents, in the event of breakage of the casing, parts of the casing, such as glass fragments, from getting between the products unnoticed.

Preferably, infrared radiators of the so-called short-wave type and/or the so-called fast medium-wave type are used. These types of infrared radiators will be explained in more detail hereinbelow.

In an advantageous embodiment, a baking apparatus according to the invention is characterized in that the monitoring means comprise detection means for detecting, during use, the electric power taken up by an infrared radiator and/or current passing through an infrared radiator. Preferably, the detection means comprise a measuring transducer for measuring the power taken up by an infrared radiator and/or the intensity of the current passing through an infrared radiator. Indeed, in the event of breaking of the casing, the gastightness will be lost and the spiral filament will burn through quickly, due to the oxygen present in the ambient air. Through detection or measuring of the power taken up or the current intensity, it is achieved that the burning-through of the spiral filament can be determined, so that breakage of the casing can be monitored. Through the use of detection, it is readily detected whether or not any power is taken up, or whether or not there passes a current. Measuring has the advantage that intermediate conditions can be established as well, for instance a deviation of the power actually taken up relative to a power that is desirably taken up.

In another embodiment, a baking apparatus according to the invention is further characterized in that it comprises interruption means for interrupting the travel of the products along the conveyor track and control means for interrupting the travel of the products by the interruption means when glass breakage is monitored by the monitoring means. It is thus provided that each time when a casing is broken, the baking apparatus can at least be partially cleaned and that fragments and possibly contaminated products can be removed from the conveyor track.

In yet another embodiment, a baking apparatus according to the invention is characterized in that it further comprises collecting means, disposed between the conveyor track and the infrared radiators, for collecting the parts of a casing in the event of breaking of the casing. It is thus provided that the chance of fragments mixing with at least the products intended for consumers is reduced considerably.

The invention also relates to a method for baking an edible product, in particular a piece of meat, by means of at least one electric infrared radiator, wherein during a first step, the intensity of the infrared radiator is controlled so that per unit of time, more radiation energy is supplied to the surface of the product than can be transmitted to the interior of the product, and wherein during a second step, the intensity of the infrared radiator is controlled so that per unit of time, at the most as much radiation energy is supplied to the surface of the product as can be transmitted to the interior of the product. Preferably, an electric spiral filament disposed in a gastight environment is used, and the temperature of the surface of the product is measured and further, depending on the temperature measured, the intensity of the infrared radiation is controlled. Thus, it is not only achieved that the product can be provided with an attractive outer layer, but also that a thin outer layer of the product can at least be partially seared up, whereby evaporation of moisture from the interior can be prevented. This reduces the weight decrease of the product during baking, which results in a lower cost price per unit of weight of the finished product.

Further elaborations of advantageous embodiments of the baking apparatus and the method according to the invention are described in the subclaims.

BRIEF DESCRIPTION OF THE DRAWINGS

The invention will hereinafter be specified with reference to an exemplary embodiment shown in a drawing. In the drawing.

DETAILED DESCRIPTION OF THE INVENTION

It is observed that the Figures are only schematic representations of preferred embodiments of the invention. In the Figures, identical or like parts are designated by corresponding reference numerals.

Figure 1:
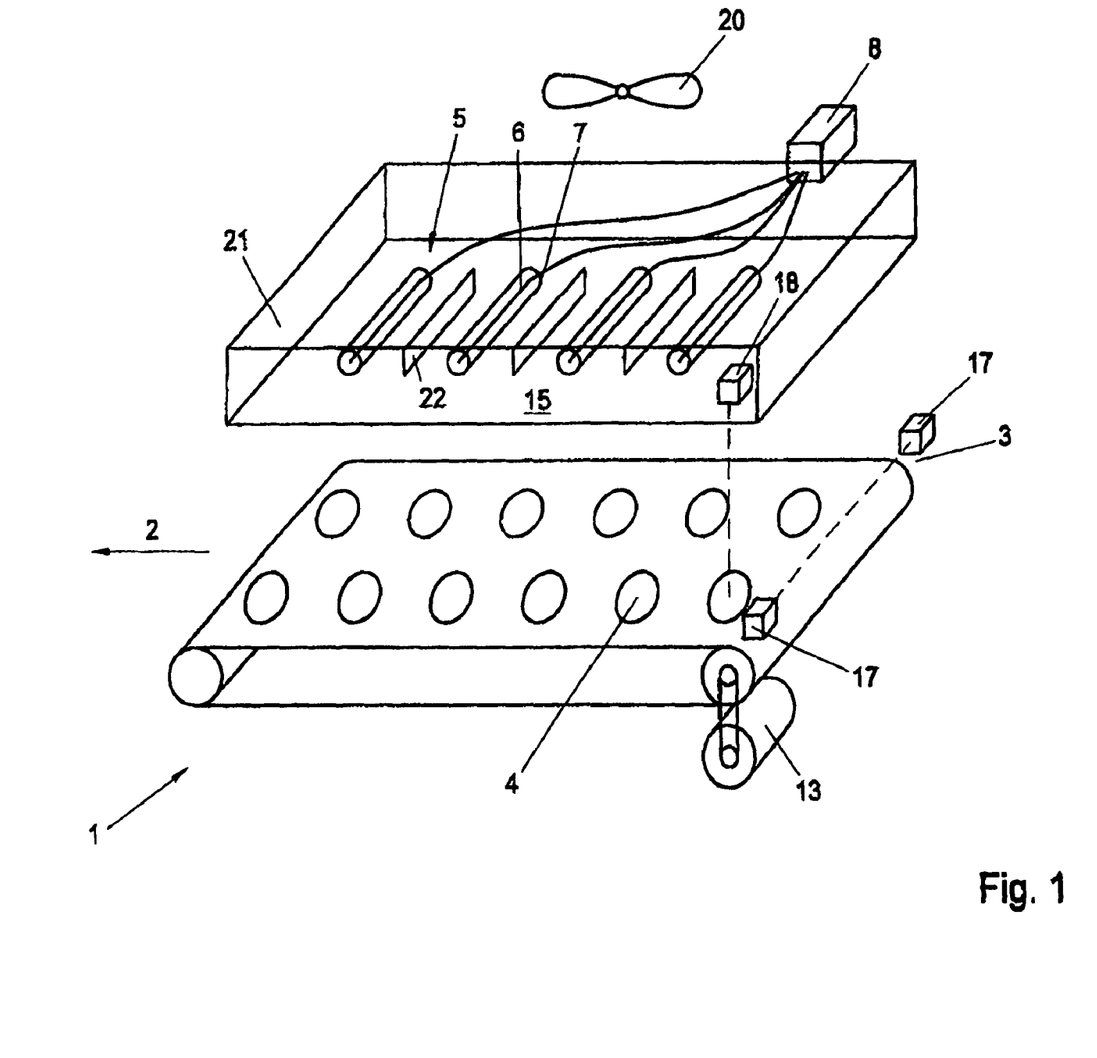
FIG. 1 is a schematic representation of a first embodiment of a baking apparatus.
Figure 2:
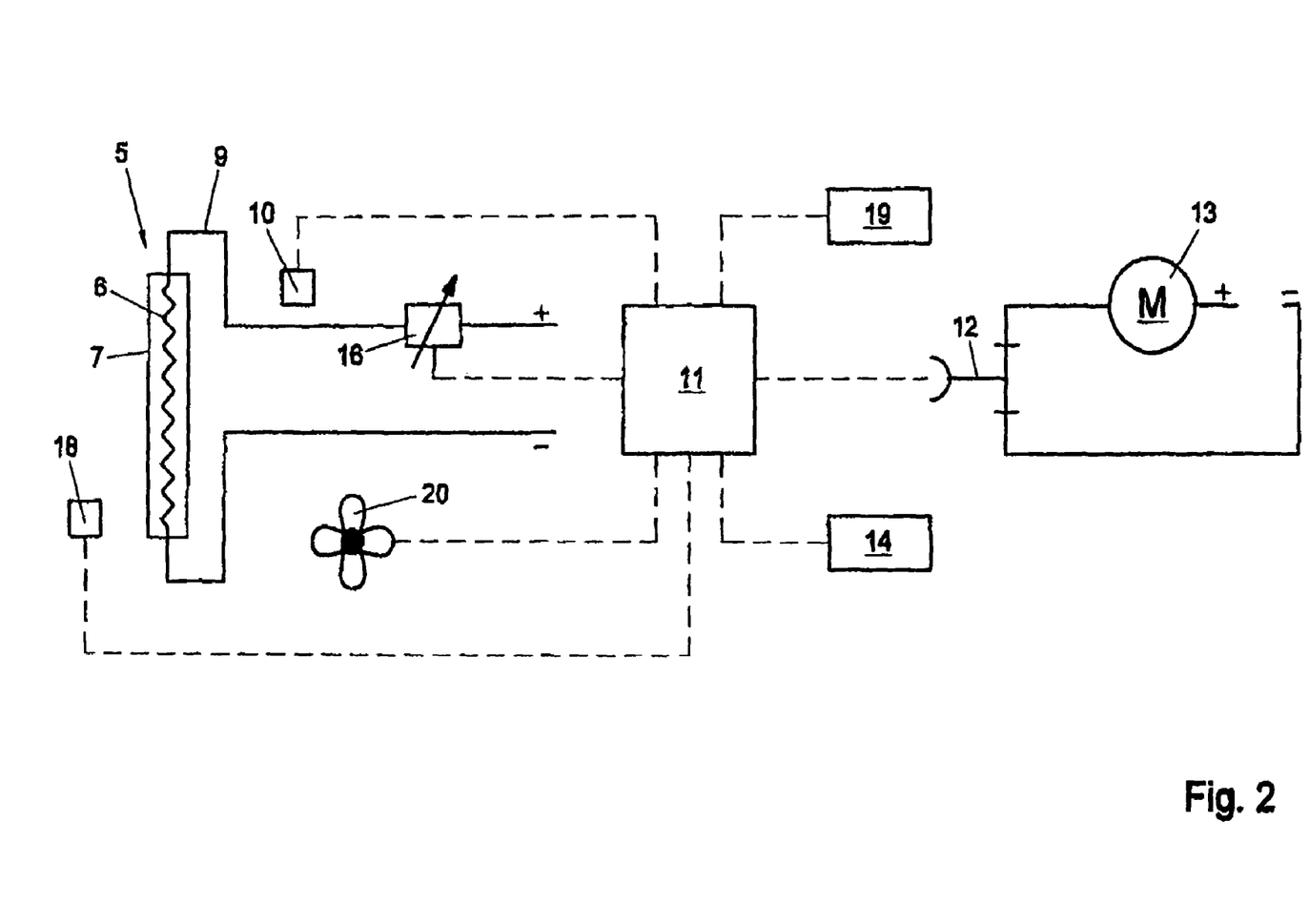
FIG. 2 is a diagram showing a number of functions of the baking apparatus of FIG. 1.

With reference to FIGS. 1 and 2, a baking apparatus 1 is schematically shown therein for baking edible products 4 which travel in a direction of travel 2 along a conveyor track 3 designed as an endless conveyor belt. Arranged above the conveyor track 3 are a number of electric infrared radiators 5. The infrared radiators are each provided with a spiral filament 6 having a gastight, infrared radiation-transmitting, breakable casing 7. The baking apparatus 1 comprises monitoring means 8 for monitoring breakage of the casings 7. The monitoring means 8 are here designed as transducers 10 provided at the electric circuit 9 for measuring, through induction, the electric power taken up by the different infrared radiators 5. Of course, the transducers may also be incorporated into the electric circuit. The transducers 10 are connected to control means 11 designed as, for instance, a PLC. By the control means 11, interruption means 12 can be actuated for interrupting the travel of the products 4. The interruption means 12 are here designed as a relay which interrupts the current to the electric drive motor 13 of the conveyor belt 13.

In the case of breakage of a casing 7, the spiral filament 6 will be exposed to the ambient air. Due to the reaction with the oxygen present in the ambient air, the spiral filament 6 will quickly burn through and no longer conduct any current, which is expressed in a decrease of the electric power taken up by the infrared radiator 5. If such decrease occurs, this is monitored by the monitoring means 8 and transmitted to the control means 11. Next, the control means 11 actuate the interruption means 12, causing the travel of the products 4 to be interrupted. Preferably, the current supply to the infrared radiators 5 is interrupted as well. Now, the radiator 4 whose spiral filament 6 is broken can be replaced. If the casing 7 is broken, possibly contaminated products 4 are removed from the conveyor track 3 and, subsequently, the portion of the conveyor track 3 located adjacent the radiator 4 is cleaned. Then, by the control means 11, the travel of the products 4 can be continued again and the current supply can be restored.

The measuring transducers 10 can also be coupled to indicating means 14 for indicating an infrared radiator 5 with a broken casing 7. The indicating means can, for instance, be designed as a lamp or a display.

Between the conveyor track 3 and the infrared radiators 5, collecting means 15 may be disposed for receiving parts of a casing 7 in the case of breakage thereof. The collecting means 15 can be designed as a plastic film, preferably a film having a low absorption of infrared radiation. A suitable film is, for instance, the polyamide film of DuPont® commercially available under the tradename Kapton®.

Preferably, the casings 7 are elongated and extend substantially transverse to the direction of travel 2. The effect thus achieved is that when a casing 7 is broken, the conveyor track 3 is possibly fouled with fragments over a limited part of its length only. It is observed that in such arrangement, it is not necessary that the products 4 travel linearly along the conveyor track 3. The conveyor track 3 may, for instance, be circular, while the infrared radiators 5 may be arranged in radial direction. A second advantage achieved by the arrangement transverse to the direction of travel 2 is that the radiators 5 form a radiation field in which any inhomogeneities in the intensity of the field lie in the direction of travel 2, so that each product 4, when traveling through the radiation field, in principle receives the same amount of radiation.

The baking apparatus 1 can further comprise regulating means 16 for regulating the intensity of the infrared radiators 5. The intensity can, for instance, be regulated for each infrared radiator 6 separately or for a group of radiators 5 by means of electronic power regulators cooperating with the control means 11.

Detection means 17 can also be arranged along the conveyor track 3 for detecting, during use, whether a product 4 is present at a given location. Such detection means 17 can, for instance, be designed as a light source cooperating with a photocell. By coupling the detection means 17 to the control means 11, it can be effected that an infrared radiator 5 is switched off when no product 4 has been present for some time. In this manner, much energy can be saved. Of course, it may be advantageous to couple the detection means forwards to the control, so that the infrared radiators can be activated already before the passing of a product, for instance for compensating the beating-up time.

The baking apparatus 1 can also be provided with measuring means 18 for measuring, during use, the temperature of a product 4. Such measuring means 18 can advantageously be designed as contactless pyrometers whereby the temperature of the surface of a product 4 can be measured. Such pyrometers are of standard commercial availability and are hence not further specified here.

Through coupling of the measuring means 18 to the control means 11, it can advantageously be effected that when a product 4 is detected by the detection means 17 and when, by the measuring means 18, the temperature of the product 4 is measured, the intensity of one or more of the infrared radiators 5 is regulated by the regulating means 16, depending on a set value. Such value can, for instance, depend on the type of product 4 or on the processing which a product 4 has to undergo, and can, for instance, be stored in a memory 19 coupled to the control means 11. In this manner, the degree of cooking of a product 4 can be accurately controlled and energy can be saved.

By means of such baking apparatus 1, during a first step, the intensity of the infrared radiator can be controlled in such a manner that per unit of time, more radiation energy can be supplied to the surface of a product than can be transmitted to the interior of the product. Such first step can be carried out adjacent the beginning of the conveyor track 8. By simultaneously measuring the temperature of the surface of the product, a thin layer of the outer surface of the product can be seared up to prevent loss of moisture during the further baking process. Due to the fast controllability of the infrared radiator 5, the outer layer of a product may be prevented from burning. During a second step, the intensity of the infrared radiator can be controlled in such a manner that at the most as much radiation energy is supplied to the surface of the product as can be transmitted to the interior of the product. It is thus effected that the product can subsequently be heated up as quickly as possible without involving any loss of moisture. By turning the product, the lower part of the surface of the product can be turned up, allowing it to be seared up as well.

In the baking apparatus 1, infrared radiators 5 of the so-called short-wave type or the so-called fast medium-wave type are preferably used. Such infrared radiators are characterized by a relatively short beating-up time during switching on and a relatively short cooling-down time during switching off. Depending on the type of infrared radiator, the heating-up time can vary from less than 15 seconds to even less than 1 second.

Hereinbelow, an explanation of the infrared radiators will be given. It may be understood that this explanation serves by way of illustration only.

An infrared radiator of the short-wave type has a shorter heating-up time and a higher end temperature of the spiral filament than a radiator of the fast medium-wave type. During heating up, the temperature of the spiral filament of an infrared radiator of the fast medium-wave type rises from, for instance, less than 100° C. t> a maximum of about 1500-1700° C. in about 4 seconds. With an infrared radiator of the short-wave type, the maximum temperature of about 1900-2100° C. is, for instance, realized within 1 second.

For an infrared radiator 5 of the fast medium-wave type, the maximum intensity of the infrared radiation lies in the medium-wave infrared range, i.e. radiation of a wavelength approximately between 1.4 and 2.5 µm, in particular about 1.5 µm. For a short-wave radiator, this lies in the short-wave infrared range, i.e. radiation of a wavelength between about 0.9 and 1.6 µm, in particular about 1.4 µm.

Depending on the type of product and the desired treatment, a particular type of infrared radiator can be selected or a combination of the radiator types can be made. Advantageous infrared radiators of the fast medium-wave type are infrared radiators of the 1400 series marketed by the firm Heraeus. Advantageous infrared radiators of the short-wave type are the infrared radiators of the 1700 series of the firm Heraeus. Such infrared radiators have a casing of quartz glass and a reflector layer applied by vaporization, so that the infrared radiation can be bundled in the direction of the conveyor track 3.

Further, the control means 11 can comprise means for registering the lighting period of a infrared radiator 5. Thus, a warning signal can be generated by the control means 11 when the chance of breaking of the casing has increased to above a given value, for instance when 90% of the expected lifetime of the infrared radiator has passed. Consequently, the chance that the infrared radiator is replaced in time, i.e. before the occurrence of breaking, becomes greater, as a result of which the chance that products intended for consumers become contaminated with parts of the casing is further reduced.

The baking apparatus 1 can also be provided with means 20 for generating an air flow between the infrared radiators 5, for instance a fan. The effect thus achieved is that the air around the infrared radiators 5 is evenly distributed, so that the infrared radiators 5 cannot only be cooled, but the radiation emitted by the infrared radiators 5 can also be distributed over the radiation area more evenly. As a result, uneven discoloring of the surface of the product to be baked can be prevented. This is important in particular during the baking of light-colored products, such as filets of chicken. Preferably, the radiators 5 are accommodated in a light box 21. The light box 21 can advantageously be provided with partitions 22 for distributing the air flow along the different radiators 5. If necessary, on the side facing the conveyor track 3, the light box can be shut off by means of the above-mentioned plastic film.

Figure 3:
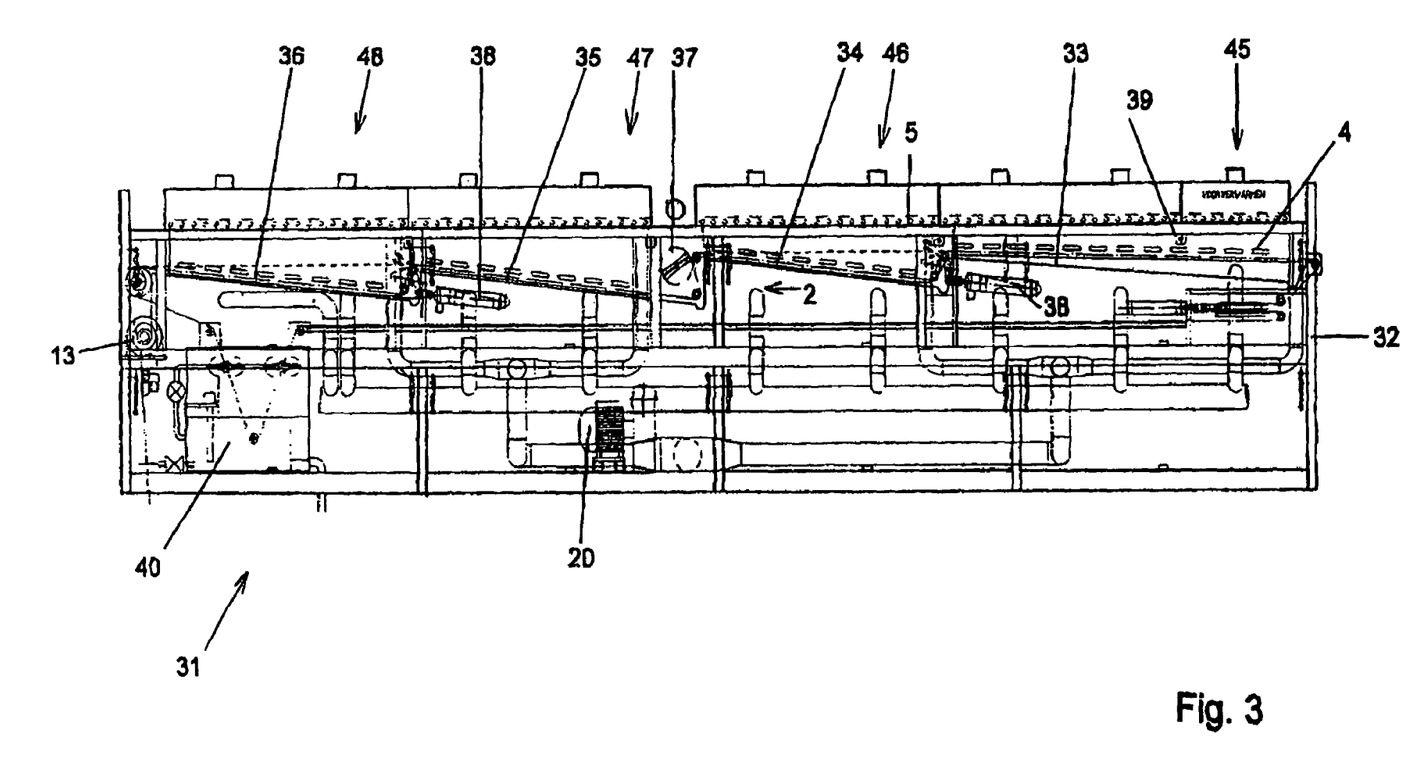
FIG. 3 is a schematic longitudinal section of a second embodiment of a baking apparatus.

FIG. 3 shows an embodiment of the baking apparatus 30 for baking edible products 4 traveling along a conveyor track 3 in a direction of travel 2, wherein the conveyor track is designed as an endless conveyor belt 31 having a tunnel-shaped housing 32 which surrounds the conveyor belt 31. The conveyor belt 31 comprises four parts 33, 34, 35 and 36. Arranged between the parts 34 and 35 is a turning station 37 for turning the products 4, for instance when the product 4 is a hamburger to be baked on two sides. Arranged between the parts 33 and 34 and the parts 35 and 36 respectively are operating cylinders 38 whereby a height difference can be set between the parts 33 and 34 and the parts 35 and 36 respectively. It is thus effected that smaller products, such as shoarma meat, can be turned more often. To enhance coloring of the products, a slight amount of oil can be sprayed onto the products by means of a tubular atomizer 39. There is further provided a washing installation 40 for washing the return part of the conveyor belt 31 during the return travel. Preferably, directly upstream of the washing installation 40, a blower is arranged for blowing the conveyor belt clean.

By means of the baking apparatus 30, the products 4 can, for instance, be seared up at their upper surfaces by means of a first group of radiators 45 and cooked by means of a second group of radiators 46. After turning of the products 4 by means of the turning station 37, the products can be further seared up by a third group of radiators 47 and further cooked by a fourth group of radiators 48. It is observed that it may be advantageous to wholly sear up the products 4 directly, for instance by turning the products earlier and searing them up on two sides before the interior is cooked.

The temperature of the surface of the products 4 can be measured by means of pyrometers arranged adjacent the places where the surface of the products is seared up, i.e. at the first group of radiators 45 and downstream of the third group of radiators 47. By means of the pyrometers disposed adjacent the third group of radiators 47, it is also possible to determine the degree of cooking on the basis of the temperature directly after turning. Adjacent the fourth group of radiators 48, a final measuring of the surface temperature can take place for checking the degree of cooking.

Figure 4:
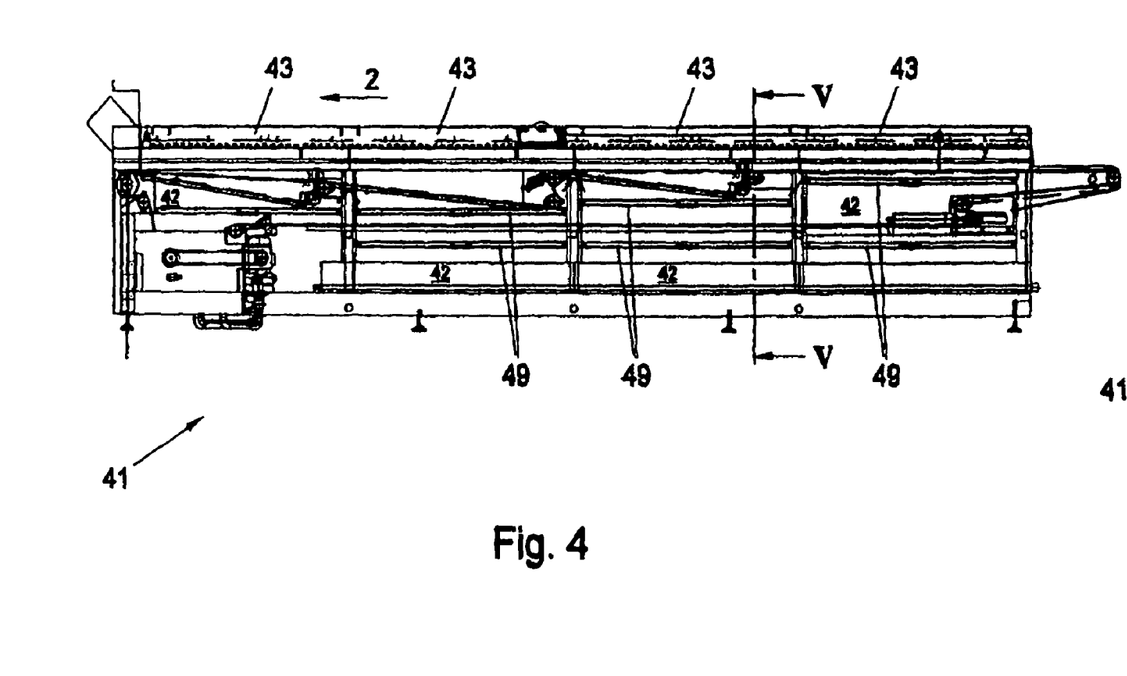
FIG. 4 is a schematic side elevation of a third embodiment of a baking apparatus.
Figure 5:
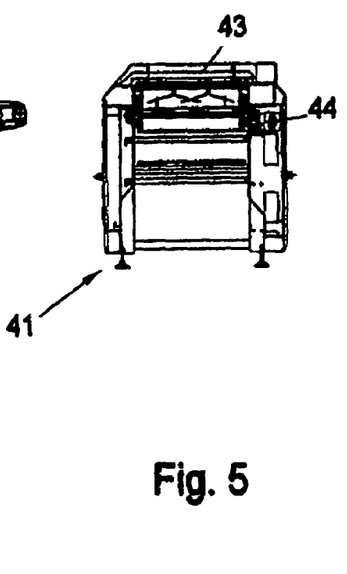
FIG. 5 is a cross section of the baking apparatus of FIG. 4, taken on the line V-V.

Referring to FIGS. 4 and 5, a baking apparatus 41 is shown therein having a tunnel-shaped housing built up from segments 42. The segments 42 are each provided with a cover part 43 supporting a number of infrared radiators 5. The cover part 43 is pivotable relative to an axis 44 extending substantially in direction of travel 2, so that the cover part is pivotable between a first position in which the radiators 5 are located above the conveyor track 3 and a second position in which the radiators 5 are accessible for maintenance operations. On a vertical side thereof, the segments 42 are provided with side panels 45. The side panels 45 are pivotable relative to a substantially vertical pivotal axis between a first position in which the tunnel-shaped housing 32 is closed off so as to be radiation-proof, and a second position in which the interior of the segment is released. Thus, in the second position, the interior of the segment is accessible. The effect thus achieved is that when the casing 7 of a radiator 5 located in the cover part 43 of a segment 42 is broken, the products present in that segment can be removed and the interior of the segment 42 can be cleaned.

Disposed between the upper part and the lower part of the conveyor belt are plate-shaped elements 49 for collecting juices released from the products 4 during baking. The plate-shaped elements 49 can, for instance, be included as a drawer in the interior of the segments, so that they can be pulled out for cleaning. Preferably the plate-shaped elements 49 slop downwards, so that a film of water can flow over the elements 49 for discharging the released juices.

It is observed that the invention is not limited to the above-described preferred embodiments. Many variations therefore are possible.

Thus, it is for instance possible to apply other types of monitoring means, for instance detection means for detecting an interruption of a conductor provided on the outside of the casing, for instance for breakage of the gold reflector layer applied by vaporization. It is also possible to detect the passing of casing parts by means of photocells, to scan the casing by means of waves, to measure the gas pressure in the conductor or to measure the presence/intensity of the emitted radiation. Further, it is possible to design the conveyor track differently, for instance as a chain.

These and many other variations will be directly understood by anyone skilled in the art. Such variations are considered to fall within the framework of the invention as set forth in the following claims.

The invention claimed is:

1. A baking apparatus for baking edible products located on a conveying surface, and traveling along a conveyor track, the baking apparatus comprising a number of electric infrared radiators arranged above the conveyor track, each infrared radiator comprising at least one spiral filament having a gastight, infrared radiation-transmitting, breakable casing, and further comprising:

monitoring means for monitoring breakage of at least one of the casings;

interruption means for interrupting the travel of the products along the conveyor track;

control means for interrupting the travel of the products by the interruption means when glass breakage is monitored by the monitoring means; and indicating means for indicating which infrared radiator has a broken casing.

2. A baking apparatus according to claim 1, wherein the monitoring means comprise detection means for detecting, during use, electric power taken up by an infrared radiator and/or current passing through an infrared radiator.

3. A baking apparatus according to claim 2, wherein the detection means comprise a measuring transducer for measuring the magnitude of the electric power taken up by an infrared radiator and/or the intensity of the current passing through an infrared radiator.

4. A baking apparatus according to claim 1, further comprising collecting means, disposed between the conveyor track and the infrared radiators, for collecting parts of a casing in the event of breakage of said casing.

5. A baking apparatus according to claim 1, wherein the collecting means comprise a plastic film.

6. A baking apparatus according to claim 1, wherein the casings are substantially elongated and extend substantially transverse to the direction of travel of the products.

7. A baking apparatus according to claim 1, wherein the infrared radiators are spaced apart in direction of travel of the products.

8. A baking apparatus according to claim 1, further comprising regulating means for regulating the intensity of one or more of the infrared radiators.

9. A baking apparatus according to claim 1, further comprising detection means for detecting, during use, whether a product is present at a particular location.

10. A baking apparatus according to claim 1, further comprising measuring means for measuring, during use, the temperature of a product.

11. A baking apparatus according to claim 1, further comprising control means for, when a product is detected by the detection means and the temperature of the product is measured by the measuring means, controlling the intensity of one or more of the infrared radiators, depending on a set value.

12. A baking apparatus according to claim 1, further comprising means for generating an air flow between the infrared radiators.

13. A baking apparatus according to claim 1, further comprising a tunnel-shaped housing surrounding the conveyor track.

14. A baking apparatus according to claim 13, wherein the housing is built up from segments, said segments each comprising at least one cover part which supports a number of infrared radiators and which is adjustable between a first position in which the infrared radiators are located above the conveyor track and a second position in which the infrared radiators are accessible for maintenance operations.

15. A baking apparatus according to claim 14, wherein the segments are each on a vertical side provided with one or more side panels which are adjustable between a first position in which the housing is closed off so as to be radiation-proof and a second position in which the interior of the segment is released, such that in the second position, the interior is accessible for maintenance operations.

16. A baking apparatus according to claim 1, wherein said number of electric infrared radiators are disposed in a box.

17. A baking apparatus as defined in claim 1, further comprising means for registering a lighting period of each of said infrared radiators and for generating a warning signal when the chance of breaking of a casing has increased to above a given value.

18. A baking apparatus for baking edible products comprising:
   a conveyor track including a motor for transporting the edible products through the baking apparatus;
   a plurality of electric infrared radiators arranged above said conveyor track, each of said radiators including at least one spiral filament contained within a glass casing;
   a plurality of monitoring transducers, each of said transducers being electrically connected to a respective infrared radiator for detecting a breakage of at least one glass casing by measuring through induction the electric power taken up by said respective radiator;
   a plurality of indicating lamps, each of said indicating lamps being in electrical communication with a respective monitoring transducer for indicating breakage of said respective radiator;
   a controller in communication with each of said transducers;
   a relay in communication with said controller and said conveyor track motor for stopping said motor upon detection of a breakage of said glass casing by said respective monitoring transducer.

19. A baking apparatus as defined in claim 18, further comprising means for registering a lighting period of each of said infrared radiators and for generating a warning signal when the chance of breaking of a casing has increased to above a given value.

20. A baking apparatus for baking edible products comprising:
   a conveyor track including a motor for transporting the edible products through the baking apparatus;
   a plurality of electric infrared radiators arranged above said conveyor track, each of said radiators including at least one spiral filament contained within a glass casing;
   a plurality of monitoring transducers, each of said transducers being electrically connected to a respective infrared radiator for detecting a breakage of at least one glass casing by measuring through induction the electric power taken up by said respective radiator;
   a controller in communication with each of said transducers;
   a relay in communication with said controller and said conveyor track motor for stopping said motor upon detection of a breakage of said glass casing by said respective monitoring transducer.

21. A baking apparatus as defined in claim 20, further comprising means for registering a lighting period of each of said infrared radiators and for generating a warning signal when the chance of breaking of a casing has increased to above a given value.

* * * * *

UNITED STATES PATENT AND TRADEMARK OFFICE
CERTIFICATE OF CORRECTION

PATENT NO.       : 7,231,871 B1
APPLICATION NO.  : 10/203466
DATED            : June 19, 2007
INVENTOR(S)      : Wilhelmus Johannes E. M. Wilbers Page 1 of 1

It is certified that error appears in the above-identified patent and that said Letters Patent is hereby corrected as shown below:

IN THE SPECIFICATION:

| | | |
|---|---|---|
| Column 1 line 42, | now reads "cat" | should read --cannot-- |
| Column 4, line 61, | now reads "radiator 6 separately" | should read --radiator 5 separately-- |
| Column 5, line 8, | now reads "the beating-up time" | should read -- the heating-up time -- |
| Column 5, line 33, | now reads "track 8" | should read --track 3-- |
| Column 5, line 51, | now reads "short beating-up time" | should read --short heating-up time-- |

Signed and Sealed this

Fourth Day of September, 2007

JON W. DUDAS
*Director of the United States Patent and Trademark Office*